United States Patent [19]

Arnesen

[11] Plant 4,455

[45] Aug. 28, 1979

[54] AZALEA NAMED VARIEGATED DOGWOOD

[75] Inventor: Richard A. Arnesen, Northridge, Calif.

[73] Assignee: Geo. J. Ball, Inc., West Chicago, Ill.

[21] Appl. No.: 912,560

[22] Filed: Jun. 5, 1978

[51] Int. Cl.[2] ..... A01H 5/00

[52] U.S. Cl. ..... Plt./55

[58] Field of Search ..... Plt./55-56

*Primary Examiner*—Robert E. Bagwill

*Attorney, Agent, or Firm*—Chas. W. Rummler

[57] ABSTRACT

A new variety of hybrid azalea particularly characterized by its variegated White and Camellia Rose flowers, portions of which have Tyrian Purple blotches extending from the flower throat to provide rich, bright and very attractive blossoms, and by its prolific branching tendencies and floriferous habit which makes it especially suitable for greenhouse forcing.

3 Drawing Figures

BACKGROUND OF THE NEW PLANT

This new variety of azalea plant was discovered by me in September 1971 as a sport of the variety Dogwood (U.S. Plant Pat. No. 3,093) grown in greenhouse at San Fernando, Calif., and the extraordinary variegated coloration of its flowers caused me to then and there proceed to reproduce this sport by means of cuttings. Subsequent propagation of this new plant through many successive generations, by means of cuttings, has demonstrated that it has other valuable characteristics all of which hold true from generation to generation and appear to be firmly fixed. This variety is now being propagated on a commercial scale in Oregon, as well as at San Fernando, Calif., and marketing of this plant has been carried on since November 1977.

DESCRIPTION OF THE DRAWING

My new azalea variety is illustrated by the accompanying photographic drawings, the first sheet showing a potted plant in full bloom, and the second sheet being a print showing face views of typical specimens of the flowers, the second sheet of drawings having been hand-painted to show the true flower colors.

DESCRIPTION OF THE NEW PLANT

The following is a detailed description of my new variety of azalea plant with color designations according to the Robert F. Wilson Horticultural Colour Chart published by The Royal Horticultural Society of London, England, in collaboration with The British Colour Council.

THE PLANT

Origin: Sport.
Parentage: "Dogwood", U.S. Plant Pat. No. 3,093.
Classification:
*Botanic.*—Rhododendron.
*Commercial.*—Hybrid Azalea.
Form: Spreading bush.
Height: Medium.
Growth: Vigorous, sturdy and generally upright.
Branching: Well branched, with prolific branching tendencies.
Foliage: Abundant.
*Leaf size.*—Similar to that of its parent.
*Leaf shape.*—Oblanceolate to spatulate with a mucronate apex consisting of a tiny white point.

*Texture.*—Puberulous.
*Aspect.*—Glossy.
*Ribs and veins.*—Alternately pinnate.
*Color.*—Upper side — young leaves — Scheeles Green 860/2 to 860. Older leaves — Ivy Green 0001060/2. Under side — young leaves — Spinach Green 0960/3. Veins — 0960/3. Older leaves — Spinach Green 0960/3. Veins — 0960.

THE BUD

Form: Oblanceolate and pointed.
Size: About ¾ to 1¼ inches long and about 5/16 to 7/16 inch in diameter.
Opening rate: Bud opens quickly.
Color: When sepals first divide — Rose Opal 022/2 and white variegated. When petals begin to unfurl — Rose Opal 022/2 and white variegated.
Sepals: Upstanding.
*Color.*—Inside — Pod Green 061. Outside — Pod Green 061/1.
Calyx: Shape — Funnel-shaped and deeply cleft.
*Size.*—Small.
*Aspect.*—Hairy.
*Splitting.*—Yes.
Peduncle: Erect, hairy and about ¼ inch long.
*Color.*—Pod Green 061/1, sometimes with a streak of Rose Opal 022.

THE FLOWER

Blooming habit: Naturally — once in early to mid-season Spring with profuse production of flowers.
Size of flower: Medium — about 2 to 2¼ inches in diameter and about 1¼ inches in depth.
Shape: Funnel-shaped.
Borne: In clusters of 2 to 3 flowers — occasionally 4 flowers per cluster.
Petalage: Number of petals — 5.
*Arrangement.*—Slightly imbricated.
*Form.*—Spatulate — fused at base to provide the generally funnel-like appearance of the flower.
*Texture.*—Extraordinarily thick.
*Aspect.*—Satiny.
*Color.*—Variegated white and Camellia Rose 622 at tip with 622/1 to 622/2 in the petal body, the upper three petals having a splotch of Tyrian Purple 727 extending outwardly from near the base, and each of the petals being irregularly bordered with the white. Reverse Side — Variegated white and Carmine 21/2.

*Petaloids.*—None.

Peduncle: Sturdy, erect and hairy.

*Length.*—About ¼ to ⅜ inch.

*Color.*—Pod Green 061/1 with a streak of Rose Opal 022 on upper side.

Discoloration (after full bloom): The color fades with a bluish tinge, as the flower dries.

Effect of weather: Color is lighter in hot weather.

Persistence: Flowers hang on and dry.

Disease tolerance: Plant tolerates water mold and cylindrocladium.

Fragrance: None.

Lasting quality: Excellent on plant.

REPRODUCTIVE ORGANS

Stamens: Number and arrangement — 5, occasionally 6 to 8, encircling the pistil.

*Anthers.*—Length — ⅛ inch long.

*Filaments.*—Length — About 1 to 1-3/16 inch.

*Color.*—Neyron Rose 623/3.

*Pollen.*—Color — White.

Pistils: Number — One.

*Length.*—About 1 to 1-3/16 inch.

*Stigma.*—Color — Camellia Rose 622.

Ovaries: Superior.

This new variety of hybrid azalea most nearly resembles its parent "Dogwood" in form and the variety "Gloria" (U.S. Plant Pat. No. 3,752) in color. It differs materially from other cultivated azalea varieties, particularly with respect to its prolific branching tendencies and floriferous habit, and its rich, bright variegation and disease tolerance make it especially suitable for greenhouse forcing. Also, the flowers are more stable than those of the Schame varieties and have an excellent lasting ability.

I claim:

1. A new and distinct variety of hybrid azalea substantially as herein shown and described, characterized by its prolific branching tendencies and floriferous habit, the bright Camellia Rose, white and Tyrian Purple variegation of its flowers, and the excellent lasting ability of the blooming plant.

* * * * *

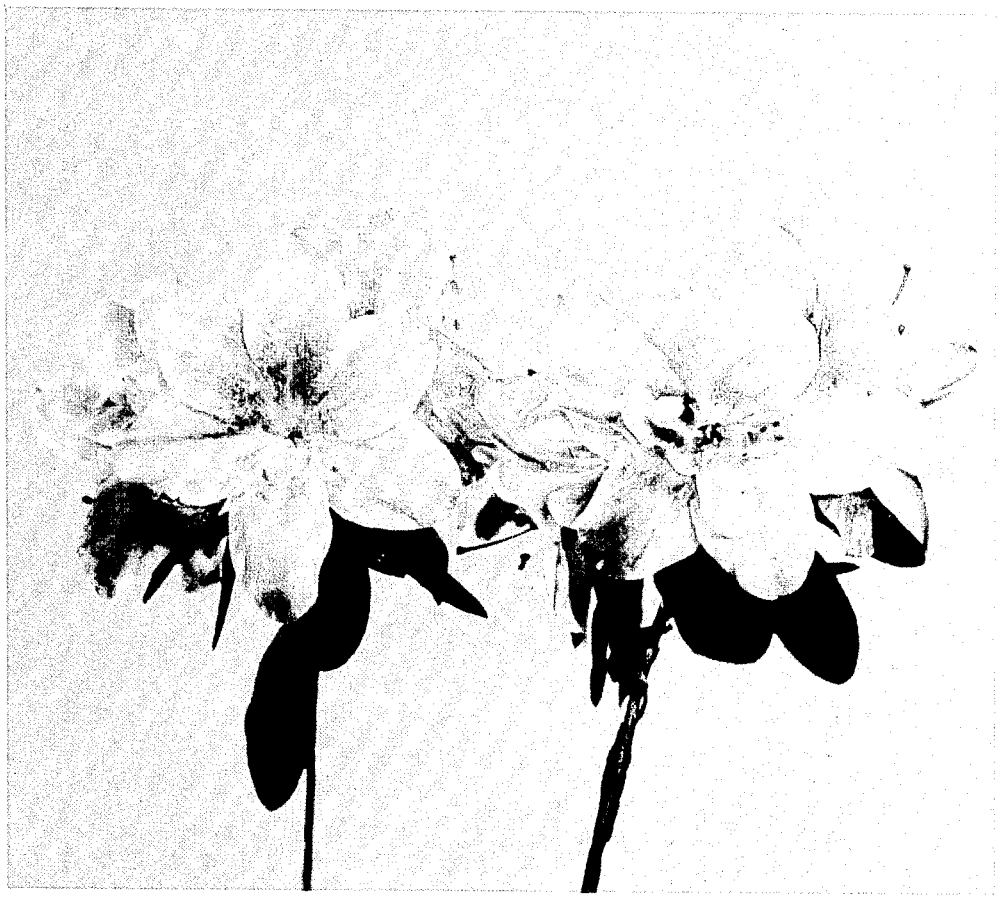

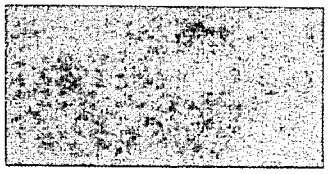

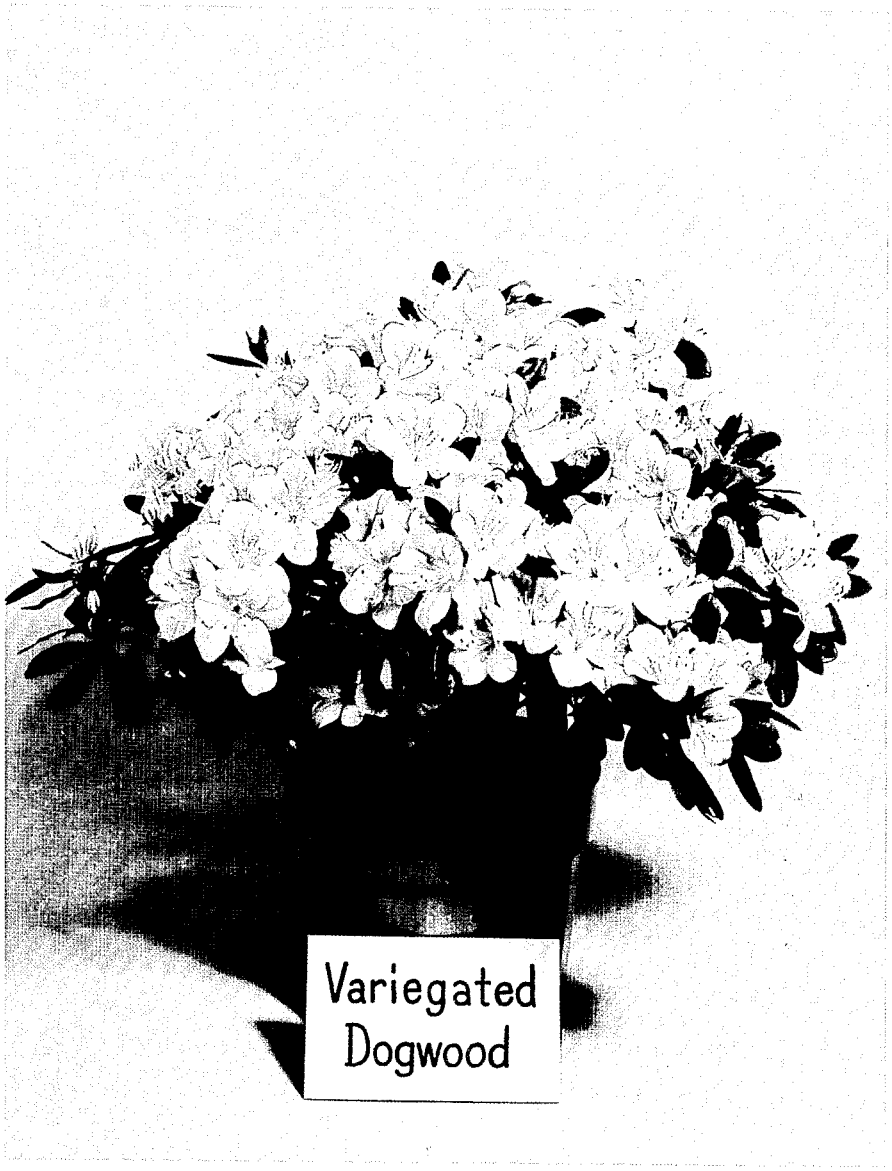
Variegated
Dogwood